(12) United States Patent
Zander

(10) Patent No.: US 11,586,055 B2
(45) Date of Patent: Feb. 21, 2023

(54) NEUTRAL CYLINDER REFRACTOR

(71) Applicant: Nathaneil Scott Zander, Moscow, ID (US)

(72) Inventor: Nathaneil Scott Zander, Moscow, ID (US)

(73) Assignee: Nathaniel Scott Zander, Ogden, UT (US)

( * ) Notice: Subject to any disclaimer, the term of this patent is extended or adjusted under 35 U.S.C. 154(b) by 405 days.

(21) Appl. No.: 16/936,342

(22) Filed: Jul. 22, 2020

(65) Prior Publication Data

US 2021/0033885 A1 Feb. 4, 2021

Related U.S. Application Data

(60) Provisional application No. 62/922,171, filed on Jul. 29, 2019.

(51) Int. Cl.
*G02C 7/02* (2006.01)
*A61B 3/04* (2006.01)

(52) U.S. Cl.
CPC ............. *G02C 7/022* (2013.01); *G02C 7/028* (2013.01); *A61B 3/04* (2013.01)

(58) Field of Classification Search
CPC .......... G02C 7/022; G02C 7/02; G02C 7/028; A61B 3/04; A61B 3/036

USPC ............ 351/159.01, 159.07, 159.22, 159.46, 351/159.52, 227
See application file for complete search history.

(56) References Cited

U.S. PATENT DOCUMENTS

| | | | | |
|---|---|---|---|---|
| 3,623,800 A | * | 11/1971 | Volk | B24B 13/065 351/159.21 |
| 3,751,138 A | * | 8/1973 | Humphrey | B29D 11/00855 359/708 |
| 3,822,932 A | * | 7/1974 | Humphrey | G02B 13/08 359/710 |
| 3,903,218 A | * | 9/1975 | Humphrey | B29D 11/00019 425/808 |
| 2015/0313463 A1 | * | 11/2015 | Trumm | A61B 3/103 351/246 |
| 2020/0029805 A1 | * | 1/2020 | Seesselberg | A61B 3/103 |
| 2020/0229693 A1 | * | 7/2020 | Piper | A61B 3/1035 |

* cited by examiner

*Primary Examiner* — William R Alexander

(57) ABSTRACT

The present invention is a neutral cylinder refractor, which is a refractor that uses spherical power in combination with cylinder lenses to render them spherically neutral. Every cylinder lens in the refractor, excluding the Jackson Cross Cylinder, has corresponding spherical power added to it to neutralize the spherical equivalent of the cylindrical lenses. The invention can be used to measure the refractive error of a patient's eye, and specifically the cylinder aspect can be measured more easily due to a lack of interference from spherical equivalent.

3 Claims, 2 Drawing Sheets

FIG. 2

| Cylinder | Sphere | Cylinder | Sphere |
|---|---|---|---|
| 0.00 | 0.00 | 0.00 | 0.00 |
| + 0.25 | − 0.125 | − 0.25 | + 0.125 |
| + 0.50 | − 0.25 | − 0.50 | + 0.25 |
| + 0.75 | − 0.375 | − 0.75 | + 0.375 |
| + 1.00 | − 0.50 | − 1.00 | + 0.50 |
| + 1.25 | − 0.625 | − 1.25 | + 0.625 |
| + 2.50 | − 1.25 | − 2.50 | + 1.25 |
| +3.75 | − 1.875 | − 3.75 | + 1.875 |
| + 5.00 | − 2.50 | − 5.00 | + 2.50 |

# NEUTRAL CYLINDER REFRACTOR

1. CLAIM OF PRIORITY TO PROVISIONAL APPLICATION (35 U.S.C. § 119(e))

This application claims priority under 35 U.S.C. § 119(e) from provisional patent Application No. 62/922,171 filed on Jul. 29, 2020. The 62/922,171 application is incorporated herein by reference.

2. FIELD OF THE INVENTION

The invention relates generally to a refractor, sometimes referred to as a "phoropter", with neutral cylinder lenses. More specifically, the invention relates to a refractor with cylindrical lenses having integrated spherical power.

3. BACKGROUND OF THE INVENTION

A manual refractor is used to determine how a lens should be shaped to correct a patient's vision. The refractor is used by an expert in a "Subjective Refraction" eye exam, where the patient responds to the expert's questions based on the patient's subjective perception of differences between lenses. In this process, the refractor has spherical lenses to correct myopia or hyperopia (nearsightedness or farsightedness) and cylindrical lenses to correct for astigmatism. Generally, spherical lenses have rotational symmetry and focus light into a point, while cylindrical lenses focus light into a line. However, a refractor's cylindrical lens also has some spherical equivalent that will alter nearsightedness or farsightedness correction (spherical power) by changes made to correct for astigmatism.

To correct for the cylindrical lens' effect on spherical power, the combined effects of the cylindrical and spherical lenses must be taken into account.

Currently there are a number of solutions for determining the refractive error of a patient's eyes. Some of these solutions attempt to determine the level of astigmatism correction needed by patients, but these solutions fail to meet the needs of the industry because the cylinder lenses used have a significant amount of spherical equivalent, causing nearsightedness or farsightedness correction (spherical power) to become offset by changes in astigmatism correction. In order to combat this problem, it is necessary to check the spherical and cylindrical powers several times to ensure that the correct balance between sphere and cylinder has been achieved. But, this solution is deficient, because it takes much longer for the refraction expert to complete the correction and this delay can make it exceedingly more difficult for the patient to respond accurately to the expert's requests for distinctions between different lenses, especially if a patient is already struggling with the test. In addition, cylindrical lenses that have not been compensated for spherical equivalent can cause patients to indicate they require more or less cylinder power when it is actually the resulting change in spherical power inherent in the cylindrical lens that is improving their myopia or hyperopia, but not the astigmatism. This results in a lower quality outcome.

What is needed is a refractor that uses cylinder lenses in combination with spherical power to neutralize the spherical equivalent, thereby eliminating the corresponding increase or decrease in sphere power that typically goes along with the increase or decrease of cylinder power when switching between cylinder lenses for the patient. Furthermore, it is desirable to remove the risk of giving the patient too much or too little spherical power due to a needed change of the cylinder power, or of having the patient prefer an increase or decrease in cylinder power when they actually require the spherical power that is induced by the change in cylinder. Still further, needed is a refractor that does not require repeated checking of sphere and cylinder power in an effort to avoid the aforementioned problems.

4. SUMMARY OF THE INVENTION

The present invention discloses a refractor that uses cylindrical lenses having integrated spherical power to neutralize the spherical equivalent, thereby eliminating the corresponding increase or decrease in sphere power that results from the increase or decrease of cylinder power when switching between cylinder lenses presented to the patient. Furthermore, it is desirable to remove the risk of giving the patient too much or too little spherical power due to a needed change of the cylinder power, or of having the patient prefer an increase or decrease in cylinder power because they actually require the spherical power that is induced by the change in cylinder power. Still further, it is desirable to have a refractor that does not require repeated checking of sphere and cylinder power during an eye exam.

The disclosed invention advantageously fills these needs and addresses the aforementioned deficiencies by providing a set of cylinder lenses with their spherical equivalent neutralized and, thus, induce no change in spherical power when switching between them.

More specifically, the disclosed refractor has a set of cylinder lenses having spherical power for each cylinder lens that is equal to −½ times the diopters of cylinder used. These components are related by combining the powers into each lens, resulting in a set of lenses with mixed sphere and cylinder powers. Accordingly, the cylinder power and its corresponding neutralizing spherical power may be ground into the same lens. In an alternative embodiment, the combined cylinder and sphere powers can be provided by pairing in a fixed relationship a lens containing the sphere and with a lens containing the cylinder power. That is, the cylinder power and its corresponding spherical power may be separate lenses that are moved together, with the result of neutralizing the spherical equivalent of each cylinder lens that is displayed to the patient.

The disclosed device is unique when compared with other known devices and solutions because it allows the refractive expert to adjust the patient's astigmatism correction without affecting the patient's spherical correction. This can be beneficial in the following ways:

1. Adjusting the spherical power and adjusting the cylindrical power will no longer affect each other. The refraction expert need only be satisfied that the initial readings are correct. This makes refraction tests much faster, because the refractive expert will no longer need to check cylindrical and spherical powers repeatedly to ensure the correct balance has been reached.
2. The possibility of giving an incorrect amount of spherical correction to a patient is decreased. For example, if a patient desires more minus sphere power, it is not uncommon for that patient to then demonstrate a need for more minus cylinder power, as this results in an effective increase in minus sphere power. This results in a lower quality outcome, which the disclosed invention overcomes.
3. Some patients have trouble determining which lenses are an improvement. Using cylinder lenses that have spherical equivalence compensated for will result in cylinder adjustments that change only astigmatism correction and do not change nearsightedness/farsightedness correction. Removing this variability makes it easier for the patient to determine whether the astigmatism correction is beneficial or not.

The disclosed device is unique in that it is structurally different from other known devices or solutions. More specifically, the device is unique due to the use of spherical power in combination with each cylinder lens for the purpose of neutralizing the spherical equivalent induced by each cylinder lens. It does not use cross cylinders in the cylinder disk, nor does it make any adjustment to the spherical disk when cylinder is adjusted.

5. BRIEF DESCRIPTION OF THE DRAWINGS

FIG. 2 is a table of selected cylinder values and the sphere power applied to each according to the disclosed invention.

6. DETAILED DESCRIPTION OF THE INVENTION

Figure 1:
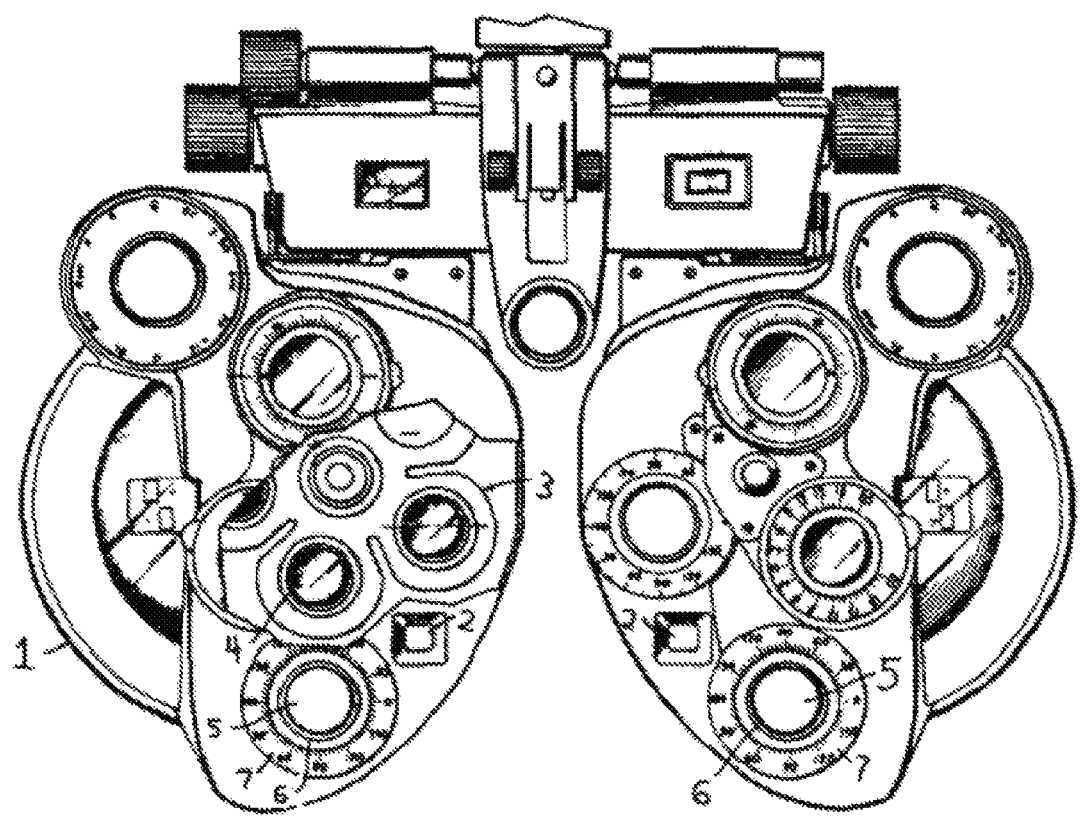
FIG. 1 shows a front view of a refractor with the assembly for testing a patient's right eye partially broken away to show the cylinder lenses.

FIG. 1 is a front view of a manual refractor from the perspective of the refraction expert performing an exam. The patient is situated on the other side of the refractor, facing the examiner. The refractor has two sets of lenses, one for the patient's right eye, seen on the left in FIG. 1, and the other for the left eye, seen on the right. A rotating disc of spherical lenses of different spherical powers 1 is used for adjusting sphere power. As shown in the cut-away portion of FIG. 1, another rotating disc 3 of cylinder lenses 4 is used to test the patient for needed astigmatism correction. A cylindrical lens control knob 5 presents the different cylinder lenses 4 to the patient. A cylinder lens display 2 shows the operator the power of the cylinder lens 4 presented to the patient. The axis of the cylindrical lenses 4 may also be adjusted by an axis knob 6, and the particular axis presented is shown by a cylinder axis indicator 7.

In an eye exam with a manual refractor, any corrections are determined empirically. For correction of myopia or hyperopia, spherical lenses of different sphere power are distributed about right and left sphere wheels, such as the right eye sphere wheel 1 shown in FIG. 1. The patient is asked whether vision is better between different sphere power lenses until the patient indicates that the most clear vision has been obtained by a particular spherical lens. To test for astigmatism, cylindrical lenses 4 of different cylindrical power are distributed about right and left cylinder wheels, such as the right eye cylinder wheel 3 shown in the cut-away section of FIG. 1. As with the subjective test with the spherical lenses, the patient is presented with cylindrical lenses 4 of different powers until the patient indicates that the most clear vision has been obtained by a particular cylindrical lens. The cylinder control knob 5 is turned to present cylindrical lenses of different powers to the patient, and the cylinder lens display 2 indicates the power of the particular cylinder lens 4 presented to the patient. Additionally, manual refractors are usually equipped with a Jackson Cross Cylinder device, which is used to determine whether the cylinder power should be increased or decreased.

Typically, the patient is first tested by looking through spherical lenses of incrementally different powers 1 and asked which provides the clearest vision. Then, cylindrical lenses of different powers 4 are presented to the patient to determine whether astigmatism correction is achieved. But, each cylindrical lens 4 has some sphere power and, as a result, the initial spherical power is no longer optimal. To address this, the expert must make changes to the sphere setting to compensate for the spherical power inherent in the cylindrical lens by adding −½ times the cylinder power to the sphere power.

The disclosed invention employs cylindrical lenses 4 in the refractor's cylinder lens wheel 3 that have been ground to incorporate spherical power that will neutralize the spherical equivalent of each cylinder lens 4. This spherical power is the opposite of the spherical equivalent of each cylinder lens 4. The amount of spherical power to be included with each lens is found by multiplying the power of the cylinder lens 4, in diopters, by −½. These components are related either by adding spherical power (diopters of the cylinder lens 4 multiplied by −½) to each cylinder lens 4 when the cylinder lens is formed or, alternatively, by providing fixed pairs of separate lenses 4 with cylindrical power and neutralizing spherical power (diopters of the cylinder lens multiplied by −½) moved in conjunction by the cylinder lens wheel 3. In either case, the result neutralizes the spherical equivalence of the neutralized cylindrical lens displayed to the patient. At the start of the refraction exam, it will be necessary to adjust the patient's prescription to fit the refractor by adding ½ times the cylinder power to the sphere power and adjusting the dials of the refractor to match the result of this calculation. At the end of the refraction exam, it will be necessary to convert back by adding −½ times the cylinder power to the sphere power, and the result of this calculation will be the patient's refractive error.

FIG. 2 shows a series of possible cylinder values (in diopters) and the corresponding sphere power that will need to be added to the cylindrical lenses in order to neutralize the spherical equivalent of the cylindrical lenses. These values are obtained by taking any cylinder value and multiplying it by −½. Combining these two powers will result in cylinder lenses that are spherically neutral.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by this disclosure. It is indeed intended that the scope of this disclosure should be determined by a proper legal interpretation and construction of the disclosure, including equivalents, as understood by those of skill in the art relying upon the complete disclosure present at the time of filing.

The invention claimed is:

1. A refractor having neutral cylinder power comprising a cylinder wheel having a plurality of cylindrical lenses, wherein each one of the plurality of cylindrical lenses has a different neutral cylindrical lens power, and wherein the neutral cylindrical lens power is obtained by adding an initial cylindrical power and a neutralizing spherical power equal to −½ times the initial cylindrical power.

2. The refractor having neutral cylinder of claim 1 wherein the neutralizing spherical power is added to the initial cylindrical power by imposing a spherical shape to each one of the plurality of cylindrical lenses.

3. The refractor having neutral cylinder of claim 1 wherein the neutralizing spherical power is added to the initial cylindrical power by fixing a neutralizing spherical lens having the neutralizing spherical power to each one of the plurality of cylindrical lenses.

* * * * *